United States Patent [19]

Szkrybalo

[11] 4,337,080
[45] Jun. 29, 1982

[54] PLANT GROWTH REGULANTS

[75] Inventor: William Szkrybalo, Verona, N.J.

[73] Assignee: Hoffmann-La Roche Inc., Nutley, N.J.

[21] Appl. No.: 733,567

[22] Filed: Oct. 18, 1976

Related U.S. Application Data

[60] Division of Ser. No. 559,209, Mar. 17, 1975, Pat. No. 4,007,206, which is a continuation-in-part of Ser. No. 335,607, Feb. 26, 1973, abandoned, which is a continuation-in-part of Ser. No. 277,538, Aug. 3, 1972, abandoned.

[51] Int. Cl.³ ............................................. A01N 43/14
[52] U.S. Cl. ............................................ 71/88; 71/75; 71/76; 71/78
[58] Field of Search ................................. 71/88, 76

[56] References Cited

U.S. PATENT DOCUMENTS 2,039,929  5/1936  Reichstein ................. 260/340.7
2,159,191  5/1939  Wenner ..................... 260/340.7
2,301,811 11/1942  Reichstein ................. 260/340.7

Primary Examiner—Catherine L. Mills
Attorney, Agent, or Firm—Jon S. Saxe; George M. Gould; John J. Maitner

[57] ABSTRACT

Plant growth regulant compounds represented by the formula:

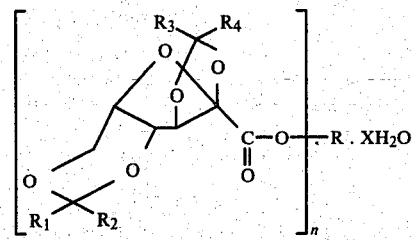

wherein, when n is 1, R is hydrogen, sodium, potassium, ammonium, substituted ammonium, straight or branched chain alkyl of from 1 to 20 carbon atoms, straight or branched chain alkenyl of from 1 to 20 carbon atoms, straight or branched chain alkynyl of from 1 to 20 carbon atoms or halo-lower alkyl and, when n is 2, R is calcium, magnesium or lower alkylene, $R_1$, $R_2$, $R_3$ and $R_4$ are hydrogen, straight or branched chain alkyl of from 1 to 7 carbon atoms, straight or branched chain alkenyl of from 1 to 7 carbon atoms, straight or branched chain alkynyl of from 1 to 7 carbon atoms, halo-lower alkyl, aryl or $R_1$ and $R_2$ together and $R_3$ and $R_4$ together are each a saturated ring containing from 3 to 8 carbon atoms, n is an integer from 1 to 2 and X is a number from 0 to 1; enantiomers and racemic mixtures.

These compounds are useful as post-emergence and pre-emergence plant growth regulants and herbicides.

31 Claims, No Drawings

PLANT GROWTH REGULANTS

RELATED APPLICATIONS

This is a division, of application Ser. No. 559,209 filed Mar. 17, 1975, and now U.S. Pat. No. 4,007,206 which is a continuation in-part of Ser. No. 335,607 filed Feb. 26, 1973 and now abandoned which, in turn, a continuation in-part of Ser. No. 277,538 filed Aug. 3, 1972 and now abandoned.

BRIEF SUMMARY OF THE INVENTION

This invention relates to plant growth regulating and herbicidal compositions as well as methods for controlling plant growth, utilizing as the active ingredients 2,3:4,6-di-O-substituted-2-keto-L-gulonic acids as well as salts and esters thereof. Preferably, the active ingredients are 2,3:4,6-di-O-isopropylidene-2-keto-L-gulonic acid, its salts and esters. This invention also relates to certain novel 2,3:4,6-di-O-substituted-2-keto-L-gulonic acids as well as novel salts and esters of 2,3:4,6-di-O-substituted-2-keto-L-gulonic acids.

DETAILED DESCRIPTION OF THE INVENTION

The compounds which are active ingredients in the compositions and methods of this invention are represented by the formula:

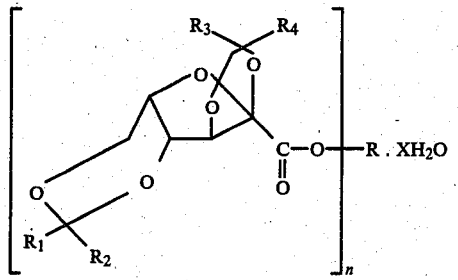

wherein, when n is 1, R is hydrogen, sodium, potassium, ammonium, substituted ammonium, straight or branched chain alkyl of from 1 to 20 carbon atoms, straight or branched chain alkenyl of from 1 to 20 carbon atoms, straight or branched chain alkynyl of from 1 to 20 carbon atoms or halo-lower alkyl and, when n is 2, R is calcium, magnesium or lower alkylene, $R_1$, $R_2$, $R_3$ and $R_4$ are hydrogen, straight or branched chain alkyl of from 1 to 7 carbon atoms, straight or branched chain alkenyl of from 1 to 7 carbon atoms, straight or branched chain alkynyl of from 1 to 7 carbon atoms, halo-lower alkyl, aryl or $R_1$ and $R_2$ together and $R_3$ and $R_4$ together are each a saturated ring containing from 3 to 8 carbon atoms, n is an integer from 1 to 2 and X is a number from 0 to 1, enantiomers and racemic mixtures.

The plant growth regulant compounds which are preferred for use in this invention because of their post-emergent plant growth regulant activity are represented by the formula:

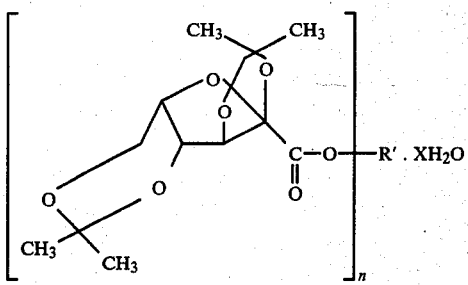

wherein, when n is 1, R' is hydrogen, sodium, potassium, ammonium, substituted ammonium, straight or branched chain alkyl of from 1 to 20 carbon atoms, straight or branched chain alkenyl of from 1 to 20 carbon atoms, straight or branched chain alkynyl of from 1 to 20 carbon atoms, or halo-lower alkyl and, when n is 2, R' is calcium, magnesium or lower alkylene, n is an integer from 1 to 2 and X is a number from 0 to 1, enantiomers and racemic mixtures.

The compounds represented by formulas I and II are all of the L configuration since they are derived from the naturally occurring ketohexose, L-sorbose. While L-sorbose is the only known naturally occurring form of sorbose, its enantiomer, D-sorbose, can be synthesized. It should be noted than compounds with the D-configuration and racemic mixtures of the compounds can be made using either D-sorbose or a mixture of D- and L-sorbose in identical preparatory procedures as for the L-configuration as discussed hereinafter.

All structural formulas set forth herein are for convenience only and are not intended to depict any absolute configuration. The formulas cover enantiomers and racemic mixtures. The Examples and other description, unless specifically noted otherwise, are directed to the racemic compounds.

The compounds represented by Formulae I and II have post-emergent and/or pre-emergent plant growth regulant activity and herbicidal activity. However, the post-emergent plant growth regulant activity is much more significant since most of the compounds have this activity and since it provides a means for control of the growth of weeds which appear in turf.

As used herein, "plant growth regulant" means a compound or composition which affects the maturation and metabolism of plants. Hence, a "plant growth regulant" has many effects on plant growth. However, not all plant growth regulant active compounds affect plants the same way. For example, they could affect vegetative growth by retarding or stimulating terminal growth, and/or stimulating side branching and could inhibit new growth such as the development of new sprouts of woody plants the sprouting of tubers and rhizomes and the development of sucker growth. Such regulants could affect flowering plants by eliminating early flowering, by thinning of blossoms or by increasing the number of flowers. Fruit-bearing trees and bushes could be affected by increases in the number, size and quality of the fruit, by producing seedless fruit, by accelerating senescence and fruit ripening. Both flowering and fruit plants could be affected by accelerating plant dormancy and maintaining bud dormancy. A "plant growth regulant" could cause selective post-emergent control of weeds by reducing their vigor and competitiveness and, thus, prevent their spread and stop normal seeding.

Some specific applications of plant growth regulants include
- preventing lodging of cereals;
- increasing production of harvestable tea leaves by promoting side branching;
- inhibiting sprouting of potatoes and onions in storage;
- suppressing growth of grass, trees, shrubs, and other vegetation in decorative lawn areas, parks, golf courses and along highways and other rights-of-way;
- accelerating fruit ripening and thus, aiding mechanical harvesting by a single or reduced number of pickings;
- defoliating cotton to permit mechanical harvest;
- inhibiting new growth of defoliated cotton and, thus, reducing staining of fiber during mechanical harvesting;
- increasing the quality of the harvested crop, e.g., sugar content of sugar cane, sugarbeets, grapefruit, grapes, and other fruits;
- aiding mechanical harvesting of nut crops by acclerating ripening, stimulating husk cracking and promoting abscission;
- protecting crops from drought;
- protecting fruit crops from frost by stimulating early dormancy and/or preventing premature breaking of dormancy;
- increasing latex flow of rubber;
- increasing frost resistance of winter cereals;
- reducing the flowering or bolting of lettuce, sugar beets and tobacco;
- controlling tobacco suckering;
- stimulating increased fruit set of soybeans, peanuts, cotton, tomatoes, melons, and other fruits and enhancing fruit color and quality;
- stimulating branching of pot plants, e.g. heather, azalea, chrysanthemum and geranium;
- growth retardation in pot plants, e.g. poinsetta, petunia chrysanthemum and azaleas;
- stimulating branching of young fruit trees, e.g. apple and pear.

"Plant growth regulant" also means the retardation of terminal (i.e., vertical) growth of plants. In grasses and weeds, this regulant activity will retard the grass height and, hence, grass growth. In bushy plants, on the other hand, the resultant retardation of terminal growth by the regulant activity often results in enhancement of lateral growth, an effect desired, e.g., in tomato plants.

As used herein, the term straight or branched chain alkyl, alkenyl or alkynyl of from 1 to 20 carbon atoms denotes a monovalent substituent consisting solely of carbon and hydrogen and which contains no aromatic unsaturation but which can be otherwise saturated or unsaturated.

As applied to these groups, the term "lower" denotes a group having a carbon skeleton containing from one to seven carbon atoms. The term "lower alkyl" includes both straight and branched chain saturated aliphatic groups containing from 1 to 7 carbon atoms, such as methyl, ethyl, n-propyl, isopropyl, n-butyl and the like. The term "lower alkylene" denotes a divalent substituent consisting of straight and branched chain aliphatic hydrocarbons of from 1 to 7 carbon atoms and having its valence bonds from different carbons. "Substituted ammonium" refers to ammonium radicals in which one or more of the hydrogens has been replaced by a lower alkyl, lower alkenyl or hydroxyalkyl substituent. The term "aryl" refers to an aromatic hydrocarbon such as phenyl and phenyl radicals having one or more alkyl, alkenyl, alkynyl, alkoxy or halo-lower alkoxy substituents thereon. "Halo-lower-alkyl" means a lower alkyl group in which one or more of the hydrogens is replaced by a halogen, preferably fluorine, chlorine or bromine.

Representative of the compounds within the scope of Formula I which are active as plant growth regulants and herbicides are:

2,3-O-isopropylidene-4,6-O-(2-chloroethylidene)-2-keto-L-gulonic acid;
2,3-O-isopropylidene-4,6-O-(1,3-dichloroisopropylidene)-2-keto-L-gulonic acid;
2,3-O-isopropylidene-4,6-O-(1,1,3-trichloroisopropylidene)-2-keto-L-gulonic acid;
2,3-O-isopropylidene-4,6-O-(1,1,1,3-tetrachloroisopropylidene)-2-keto-L-gulonic acid;
2,3-O-isopropylidene-4,6-O-(2,2-dichloroethylidene)-2-keto-L-gulonic acid;
2,3-O-isopropylidene-4,6-O-(1,1,3,3-tetrachloroisopropylidene)-2-keto-L-gulonic acid;
2,3-O-isopropylidene-4,6-O-(1,1,1,3,3-pentachloroisopropylidene)-2-keto-L-gulonic acid;
2,3-O-isopropylidene-4,6-O-(2,2,2-trichloroethylidene)-2-keto-L-gulonic acid;
2,3-O-isopropylidene-4,6-O-(1,1,1,3,3,3-hexachloroisopropylidene)-2-keto-L-gulonic acid;
2,3-O-isopropylidene-4,6-O-(2-fluoroethylidene)-2-keto-L-gulonic acid;
2,3-O-(2-butylidene)-4,6-O-isopropylidene-2-keto-L-gulonic acid;
2,3-O-(3-pentylidene)-4,6-O-isopropylidene-2-keto-L-gulonic acid;
2,3-O-(2-ethylidene)-4,6-O-isopropylidene-2-keto-L-gulonic acid;
2,3-O-isopropylidene-4,6-O-(1,3-difluoroisopropylidene)-2-keto-L-gulonic acid;
2,3-O-isopropylidene-4,6-O-(1,1,3-trifluoroisopropylidene)-2-keto-L-gulonic acid;
2,3-O-isopropylidene-4,6-O-(1,1,1,3-tetrafluoroisopropylidene)-2-keto-L-gulonic acid;
2,3-O-isopropylidene-4,6-O-(2,2-difluoroethylidene)-2-keto-L-gulonic acid;
2,3-O-isopropylidene-4,6-O-(1,1,3,3-tetrafluorisopropylidene)-2-keto-L-gulonic acid;
2,3-O-isopropylidene-4,6-O-(1,1,1,3,3-pentafluoroisopropylidene-2-keto-L-gulonic acid;
2,3-O-isopropylidene-4,6-O-(2,2,2-trifluoroethylidene)-2-keto-L-gulonic acid;
2,3-O-isopropylidene-4,6-O-(1,1,1,3,3,3-hexafluoroisopropylidene)-2-keto-L-gulonic acid;
2,3-O-isopropylidene-4,6-O-(2-bromoethylidene)-2-keto-L-gulonic acid;
2,3-O-isopropylidene-4,6-O-(1,3-dibromoisopropylidene)-2-keto-L-gulonic acid;
2,3-O-isopropylidene-4,6-O-(1,1,3-tribromoisopropylidene)-2-keto-L-gulonic acid;
2,3-O-isopropylidene-4,6-O-(2,2-dibromoethylidene)-2-keto-L-gulonic acid;
2,3-O-isopropylidene-4,6-O-(1,1,3,3-tetrabromoisopropylidene)-2-keto-L-gulonic acid;
2,3-O-isopropylidene-4,6-O-(2,2,2-tribromoethylidene)-2-keto-L-gulonic acid;
2,3-O-isopropylidene-4,6-O-(1,1,1-tribromoisopropylidene)-2-keto-L-gulonic acid.
2-keto-L-gulonic acid monohydrate;

2,3:4,6-di-O-cyclohexylidene-2-keto-L-gulonic acid;
2,3:4,6-di-O-(2-butylidene)-2-keto-L-gulonic acid;
2,3:4,6-di-O-methylene-2-keto-L-gulonic acid;
2,3-O-isopropylidene-4,6-O-methylene-2-keto-L-gulonic acid;
2,3-O-isopropylidene-4,6-O-ethylidene-2-keto-L-gulonic acid;
2,3-O-isopropylidene-4,6-O-(2-butylidene)-2-keto-L-gulonic acid;
2,3-O-isopropylidene-4,6-O-cyclohexylidene-2-keto-L-gulonic acid;
2,3:4,6-di-O-(3-pentylidene)-2-keto-L-gulonic acid;
2,3:4,6-di-O-ethylidene-2-keto-L-gulonic acid;
2,3:4,6-di-O-benzylidene-2-keto-L-gulonic acid;
2,3:4,6-di-O-(p-methoxy-benzylidene)-2-keto-L-gulonic acid;
2,3-O-isopropylidene-4,6-O-benzylidene-2-L-gulonic acid;
2,3-O-isopropylidene-4,6-O-(p-methoxybenzylidene)-2-keto-L-gulonic acid;
2,3-O-isopropylidene-4,6-O-(3-pentylidene)-2-keto-L-gulonic acid;

In addition, salts, e.g. alkaline, alkaline earth, ammonium and substituted ammonium, and esters, e.g. lower alkyl, lower alkenyl and lower alkinyl, of the above compounds are also active as plant growth regulants and herbicides.

Representative of the preferred compounds within the scope of Formula II are:
ethyl-2,3:4,6-di-O-isopropylidene-2-keto-L-gulonate;
n-butyl-2,3:4,6-di-O-isopropylidene-2-keto-L-gulonate;
n-propyl-2,3:4,6-di-O-isopropylidene-2-keto-L-gulonate;
isopropyl-2,3:4,6-di-O-isopropylidene-2-keto-L-gulonate;
n-dodecyl-2,3:4,6-di-O-isopropylidene-2-keto-L-gulonate;
n-pentyl-2,3:4,6-di-O-isopropylidene-2-keto-L-gulonate;
calcium-2,3:4,6-di-O-isopropylidene-2-keto-L-gulonate;
n-decyl-2,3:4,6-di-O-isopropylidene-2-keto-L-gulonate;
benzyl-2,3:4,6-di-O-isopropylidene-2-keto-L-gulonate;
isoamyl-2,3:4,6-di-O-isopropylidene-2-keto-L-gulonate;
2-butyl-2,3:4,6-di-O-isopropylidene-2-keto-L-gulonate;
2-bromoethyl-2,3:4,6-di-O-isopropylidene-2-keto-L-gulonate;
N-ethanolammonium-2,3:4,6-di-O-isopropylidene-2-keto-L-gulonate;
Bis-2,3:4,6-di-O-isopropylidene-2-keto-L-gulonate, ethylene glycol ester.
propargyl-2,3:4,6-di-O-isopropylidene-2-keto-L-gulonate.
2,3:4,6-di-O-isopropylidene-2-keto-L-gulonic acid monohydrate;
allyl-2,3:4,6-di-O-isopropylidene-2-keto-L-gulonate;
sodium-2,3:4,6-di-O-isopropylidene-2-keto-L-gulonate;
potassium-2,3:4,6-di-O-isopropylidene-2-keto-L-gulonate;
ammonium-2,3:4,6-di-O-isopropylidene-2-keto-L-gulonate;
dimethylammonium-2,3:4,6-di-O-isopropylidene-2-keto-L-gulonate.
methyl-2,3:4,6-di-O-isopropylidene-2-keto-L-gulonate.

The active compounds are useful in plant growth regulating compositions for controlling growth of grasses and weeds as well as other undesired plants which become inadvertently mixed in with the desired crops. While the compounds have pre-emergent growth regulant activity, they are most useful when used for post-emergent control. The post-emergent efficacy of the active compounds of this invention is apparent from their control of undesired plants. For example, in the post-emergent control of crabgrass, a weed which heretofore has not been effectively controlled by post-emergent herbicides the active compounds of this invention slow down the growth and maturation of crabgrass and by thus preventing its seeding, effectively prevent its spread.

In the control of grasses, particularly home lawns and industrial turfs, e.g. golf courses, it has been established that a maximum growth retardation as evidenced by diminished grass height as compared to an untreated control of about 40%–60% is desirable with about 50% growth retardation preferred. Any retardation less than 40% is ineffective in that grass control is not substantial enough to have a significant aesthetic effect and to reduce or eliminate manual care. On the other hand, retardation greater than 60% results in an undesired skimpy appearance to the lawn or turf with subsequent invasion thereof by weeds and other undesirable plants.

The active compounds show herbicidal activity especially against composite weeds, e.g. Matricaria species and other weeds such as *Papaver rhoeas, Stellaria media* and *Caprella bursa pastoris.*

The active compounds useful in this invention are particularly active against the following plants:

(a) grasses such as *Agropyron repens, Bromus inermis, Bromus erectus, Deschampsia flexuosa, Alopecurus pratensis, Arrhenatherum elatius, Dactylis glomerata, Festuca pratensis, Trisetum flavescens, Holcus lanatus, Lolium perenne, Poa annua, Poa neumoralis, Festuca ovina, Festuca rubra, Festuca nigrescens, Cynosurus cristatus, Agrostis schraderiana, Agrostis stolonifera, Phleum pratense, Phleum nodosum, Cynodon dactylon,* sugar cane and cereals such as corn, rice, wheat, rye, barley, oats and sorghum;

(b) trees and shrubs such as fruit trees e.g., apple, pear, peach, cherry and citrus, as well as cocoa, tea, coffee banana and rubber trees;

(c) ornamental plants such as privet, horn-beam, white cedar, juniper, rose, azalea, chrysanthemum, poinsettia, cyclamen, pyracantha, forsythia, magnolia, oleander and cotoneaster;

(d) field crops such as cotton, soya beans, peanuts, tobacco and flax;

(e) vegetable such as legumes, cucumbers and solanaceae, e.g., tomatoes;

(f) berries such as strawberries, blackberries, blueberries, cranberries, raspberries and currants.

In addition they are also useful for reducing pruning requirements or, for example, in viticulture and ornamental landscaping.

In order to effect uniform distribution of the active compound of the growth regulating compositions according to this invention, the compound can be mixed with agriculturally acceptable adjuvants conventionally used for such applications so that they may be formulated as solutions, emulsions, dispersions, dusts or wettable powders.

The term "agriculturally acceptable adjuvant" as used herein includes:

(a) agriculturally acceptable inert carrier materials as, for example, surface active agents, carriers, sticking agents, stabilizers, filler, modifiers, diluents, conditioning agents and the like and (b) other active agricultural materials such as herbicides, fungicides, insecticides, or plant growth regulants which complement the active plant growth regulant ingredient or extend the useful life of the composition.

It is understood, of course, that the adjuvant added to the abscission compositions of this invention comprises either only the inert materials of (a), the active materials of (b) or a combination of materials from (a) and (b).

Liquid formulations of the active compounds for direct spraying may be made, for example, as aqueous solutions where possible or as solutions in solvent mixtures containing acetone, methanol and dimethyl formamide (DMF) in the ratio 90:8:2, volume/volume. In the case of 2,3:4,6-di-O-isopropylidene-2-keto-L-gulonic acid, known also as DAG, buffered (pH 5–7) formulations may be prepared by the addition of potassium hydrogen phosphate to aqueous solutions containing 1% Tween 20. Such buffering is necessary in view of the known instability of DAG in aqueous solution below pH 5.

Emulsions can be prepared containing 25–50% of the active ingredient, and surface active agents, e.g., wetting agents, dispersing agents, emulsifying agents and the like, in sufficient amounts to impart the desired characteristics to the formulation.

A wettable powder premix for preparing aqueous solution comprises from about 40% to about 60% of the active ingredient and from about 60% to about 40% by weight of a surfactant.

Another typical wettable dry powder composition, preferred for use in aqueous spray formulations by dispersal in a water carrier, comprises, in percents by weight based on the total weight of the dry powder, from about 1% to about 5% of an inert diluent anti-caking agent, from about 3% to about 10% of a surfactant such as Triton B-1956, X-77 and sodium lauryl sulfate, from about 0.1% to about 1% of an anti-foaming agent such as sodium stearate, from about 0.4% to about 1.5% of a buffer to maintain the pH of the formulation in water at 8–10 and, the balance, the active ingredient of this invention. (Triton ®-1956 ® is a water-dispersible, resin-based surfactant manufactured by Rohm and Haas and X-77 (Chevron-Ortho) is a non-ionic type composition containing as the principal functioning agent alkylarylpolyoxyethylene glycols, free-fatty acids and isopropanol).

Thus, typically such a wettable dry powder composition would contain, in percents by weight based on the total weight of the dry powder, about 90% of an active compound of this invention, about 6% of sodium lauryl sulfate surfactant, about 2.5% of a silicagel anticaking agent, about 0.5% of sodium stearate antifoaming agent and about 1% of anhydrous sodium carbonate. The amount of sodium carbonate added is adjusted to provide a pH of 8–10 when the formulation is added to water.

Such dry powder formulations readily dissolve in water to form sprayable formulations containing an amount of the active ingredient of this invention which is effective as a plant growth regulant.

In addition, many of the salts and other derivatives of DAG which are water-soluble can be used alone by dissolution in water.

Several other methods can be utilized for the application of the active compounds of this invention to plants. One of these methods utilizes compositions comprising injection solutions containing the active ingredient. This composition is injected into the trunk of a tree or the stem of a woody plant or herbaceous plant either by gravity feed or under pressure. Such solution compositions contain from about 1% to about 20% by weight, based on the weight of the total composition, of the active ingredient plus such optional ingredients as surfactants and anti-friction agents. Any solvent compatible with the active ingredient and which neither interferes with the function of the active ingredient in the plant nor effects the maturation of the plant itself can be used. Water, however, is the preferred solvent.

Another method is that known as stem painting or banding wherein the active ingredient, in admixture in a paste or gel, is applied to the trunk or stem. Preferably the bark or outer covering of the trunk stem is scratched to facilitate penetration of the active ingredient into the plant and, thus, to function as a plant growth regulant. Such pastes or gels should contain from about 5% to about 30% by weight, based on the weight of the total composition, of the active ingredient. The actual chemical composition of the paste or gel component is not critical as long as it does not interfere with the penetration or function of the active ingredient, adheres to the plant's trunk or stem and does not dry or set too rapidly. Examples of acceptable pastes include lanolin, viscous oils, paints used to protect pruning wounds, animal glues, asphalt tars and water-based pastes. Lanolin is the preferred paste component.

Different forms of application may be better adapted to the various purposes for which the active compounds are to be used by the addition of substances which improve dispersion, adhesion, resistance to rain and penetrative power such as fatty acids, resins, wetting agents, emulsifying agents, glue and the like. In a similar manner, the biological spectrum may be broadened by the addition of substances having bactericidal, herbicidal, and fungicidal properties and also by combination with fertilizers, chelating agents and other plant growth regulators.

Representative of herbicides and plant growth regulants which may be admixed with the compounds of this invention are:
2,2-dichloropropionic acid
N-(4-aminobenzenesulphonyl) methylcarbamate
2-chloro-4-ethylamino-6-isopropylamino-1,3,5-triazine
4-chloro-2-oxobenzothiazolin-3-ylacetic acid
5-bromo-6-methyl-3-(1-methyl-n-propyl) uracil
3,5-dibromo-4-hydroxybenzonitrile
D-N-ethyl-2-(phenylcarbamoyloxy) propionamide
N-(4-bromo-3-chlorophenyl)-N'-methoxy-N'-methylurea
2-chloro-9-hydroxyfluorene-9-carboxylic acid
N'-4-(4-chlorophenoxy) phenyl-NN-dimethylurea
isopropyl N-(3-chlorophenyl) carbamate
2,3,5,6-tetrachloroterephthalic acid dimethyl ester (DCPA)
2,4-dichlorophenoxyacetic acid
4-isopropylamino-6-methylamino-2-methylthio-1,3,5-triazine
3,6-dichloro-2-methoxybenzoic acid
(±) 2-(2,4-dichlorophenoxy) propionic acid
9,10-dihydro-8a, 10a-diazoniaphenanthrene-2A
N'-(3,4-dichlorophenyl)-NN-dimethylurea
gibberellic acid
indolylacetic acid
indolylbutyric acid
4-hydroxy-3,5-di-iodobenzonitrile
N'-(3,4-dichlorophenyl)-N-methoxy-N-methylurea
4-chloro-2-methylphenoxyacetic acid 4-(4-chloro-2-methylphenoxy) butyric acid
(±) 2-(4-chloro-2-methylphenoxy) propionic acid
N-(benzothiazol-2-yl)-NN'-dimethylurea
N'-(3-chloro-4-methoxyphenyl)-NN-dimethylurea
1,2,3,6-tetrahydro-3,6-dioxopyridazine
N'-(4-chlorophenyl)-N-methoxy-N-methylurea
N'-(4-chlorophenyl)-NN-dimethylurea
napthylacetic acid
N-1-naphthylphtalamic acid
2,4-dichlorophenyl 4-nitrophenyl ether
1,1'-dimethyl-4,4'-bipyridylium-2A
3-(m-tolylcarbamoyloxy)phenyl carbamate
4-amino-3,5,6-trichloropicolinic acid
4,6-bisisopropylamino-2-methylthio-1,3,5-triazine
N-(3,4-dichlorophenyl) propionamide
isopropyl N-phenylcarbamate
5-amino-4-chloro-2-phenylpyridazin-3(2H)-one 2-chloro-4,6-bisethylamino-1,3,5-triazine
sodium nonochloroacetate
2,4,5-trichlorophenoxyacetic acid
5-chloro-6-methyl-3-t-butyluracil
4-ethylamino-2-methylthio-6-t-butylamino-1,3,5-triazine(terbutryn)
2,3,5-triiodobenzoic acid
1,1,4-trimethyl-6-isopropyl-5-propionyl-indane Representative fungicides which may be admixed with the compounds of this invention are:
2,4-Dichloro-6-(o-chloroaniline)-S-triazine
2,4,5,6-Tetrachloroisophthalonitrile
p-Dimethylaminobenzenediazo sodium sulfonate
1,4-Dichloro-2,5-dimethoxybenzene
Manganous-ethylene-bisdithiocarbamate
Zinc-manganous-ethylene-bisdithiocarbamate
Coordination product of zinc and manganese-ethylene-bisdithiocarbamate
Methyl-1(butylcarbamoyl)-2-benzimidazol-carbamate
2-(4-thiazol)-benzimidazol
cis-N-[(trichloromethyl)-thio]-4-cyclohexene-1,2-dicarboximide Rates of application are based upon the results reported herein and are not to be deemed all-inclusive since many extraneous factors can alter the rates of application. For example, rates may vary not only among different plant species but also within a particular species depending on such factors as plant size and age, the compound used, the time of year, type of soil and such climatological conditions at application time as air temperature, rainfall and winds. In addition, if the compounds or compositions are applied via a soil drench, higher concentrations would be needed since this type of application is indirect in comparison to a direct application, upon leaves and stems, e.g. spraying.

The amount of active ingredient in the growth regulating compositions of this invention thus varies according to the plants to be controlled, the requisite application rate, type of application the active compound used and the control desired. Generally, the compositions contain less than 50% active compound.

Basically, the application rate of the active compound is that which is effective in providing the requisite growth regulant control to the plant. For example, as noted earlier an effective growth regulant amount for grasses is that amount which will retard grass height growth to 40%–60% of the normal growth rate. Hence, the choice of the minimum application rate would be determined by the minimum amount of active compound which is effective in regulating growth to the lowest limit of the desired growth retardation range.

The choice of the maximum application rate would be determined as that amount which is effective in regulating growth to the upper limit of the desired growth retardation range, i.e., in the case of lawn and turf grasses, that amount above which a skimpy appearance to the turf or lawn results, or which prevents all subsequent growth or causes excessive undesirable chlorosis (i.e., yellowing of grass). With tomato plants, the criteria for effective growth retardant amount are different since a dwarfed, bushy plant wherein there is no loss of fruit quality or quantity is considered desirable. The parameters for effective growth regulant activity for such plants are retarded terminal growth and enhanced or non-retarded lateral growth as the minimum effects and retarded terminal and lateral growth as the maximum effects. Application rates of active compounds which have these desired effects on tomato plant growth are determined with these criteria in mind. In order to obtain the greatest post-emergent growth regulating activity, application rates of from 0.5 pound to 20 pounds or more per acre generally are needed based on the weight of the active compound. The greatest post-emergence growth regulating activity is normally obtained with application rates of from about 1 to 15 pounds or more of active ingredient per acre. A preferred dosage range in solutions for spray application is from 100 to 10,000 ppm depending on the species to be treated and the active compound utilized with the most preferred range generally being 100 to 1,000 ppm.

An additional advantage in the use of the active compounds of this invention is the absence of any permanent effect on plants or any regulant residue in the soil. As the compounds undergo slow decomposition, there is a consequent diminution of activity. Such an effect is advantageous in that (a) a short-term effect, which can be lengthened by subsequent additional application, is attained;

(b) normal growth activity resumes as the regulant activity decreases; and (c) no deleterious residues remain on the plants or in the soil.

The length of the retardant effect varies with the compound used and other factors such as the plant species, climatological conditions, etc.

Although exhibiting plant growth regulant and herbicidal activity, the active compounds are virtually non-toxic to animals. For example, no rats died when fed either DAG or its sodium salt at a rate of 4 grams per kilogram of body weight. The decomposition products, initially 2-keto-L-gulonic acid and finally carbohydrates, are also non-toxic.

It will be appreciated, of course, that all of the compounds represented by Formulas I and II are not active against all plants. However, each of the active compounds within the scope of this invention has activity against a specific plant or plants which is a function of the compound. As will be seen hereinafter, one advantage of this invention is that it provides a series of compositions which when applied to various plants as noted earlier supplies pre-emergent and post-emergent growth regulating activity and herbicidal activity on a wide spectrum of plants. Growth regulant activity of the active compounds of the instant invention is exemplified in the following microscreen test for post-emergence effects.

A. Evaluation of 2,3:4,6-di-O-isopropylidene-2-keto-L-gulonic acid, its salts and esters.

Grass retardant activity of the preferred compounds of the instant invention is exemplified in the following greenhouse screening tests for post-emergence effects especially the retardant activity on crabgrass and established Kentucky Bluegrass.

The compounds to be evaluated are dissolved in a solvent mixture of 90 parts by volume acetone, 8 parts by volume methanol and 2 parts by volume dimethyl formamide (DMF).

The crabgrass used is 10 days old and slightly less than one inch tall. Well-established Kentucky Bluegrass was clipped to about 1 inch in height just prior to evaluation of the compounds.

The compounds in solution were applied by spraying at application rates of 0.5 to 8 pounds/acre to the established crabgrass and bluegrass plots.

Plant response, i.e. growth retardation, is determined by grass height measurements and grass weight (i.e., from clippings) measurements from 11 to 26 days after spraying.

Three compounds were included as reference standards in the study. Maleic hydrazide (6-hydroxy-3-(2H)-pyrridazinone) was applied as an aqueous solution of its water-soluble concentrate (3 pounds/gallon) while two morphactins, n-butyl-9-hydroxyfluorene-(9)-carboxylate designated IT-3233 and, methyl-2-chloro-9-hydroxyfluoroene-(9)-carboxylate designated IT 3456 were applied in the solvent mixture described above.

Additional reference standards which can be used if desired include chloriflurecol (methyl-2-chloro-9-hydroxyfluorene-9-carboxylate), CCC (2-chloroethyl-trimethyl ammonium chloride), Alar (N-dimethylamino succinamic acid), 2,4-D (2,4-dichlorophenoxy acetic acid), MCPA (2-methyl-4-chlorophenoxy acetic acid), CMPP (2-methyl-4-chlorophenoxy propionic acid), ioxynil (3,5-diiodo-4-hydroxy benzonitrile) and Ethrel (2-chloroethyl phosphoric acid).

Test results are provided in the following Tables I and II.

TABLE 1

Post-Emergence Growth Retardant Activity of 2,3:4,6, di-0-isopropylidene-2-keto-L-gulonic acid (DAG) and its Derivatives

| Cpd | Rate, lbs./ Acre | Grass Height, cm. for days after application | | |
|---|---|---|---|---|
| | | Crabgrass | | Bluegrass |
| | | 11 days | 18 days | 26 days |
| Untreated Control | — | 10 | 11.7 | 7.0 |
| DAG | 8 | 1.67 | 4.0 | 3.5 |
| | 4 | 3.0 | 5.3 | 4.5 |
| | 2 | 3.8 | 7.5 | 6.0 |
| | 1 | 5.2 | 9.0 | 8.0 |
| | 0.5 | 7.2 | 11.3 | 7.0 |
| DAG Methyl ester | 8 | 2.3 | 3.3 | 3.0 |
| | 4 | 3.5 | 6.7 | 5.0 |
| | 2 | 5.5 | 10.8 | 6.0 |
| | 1 | 7.0 | 11.8 | 7.5 |
| | 0.5 | 10.2 | 12.3 | 7.0 |
| DAG Ethyl ester | 8 | 2.2 | 6.3 | 6.0 |
| | 4 | 4.3 | 8.3 | 7.5 |
| | 2 | 8.2 | 10.8 | 7.5 |
| | 1 | 9.5 | 11.8 | 6.5 |
| | 0.5 | 11.5 | 12.3 | 6.5 |
| DAG n-butyl ester | 8 | 3.0 | 4.7 | 5.0 |
| | 4 | 3.7 | 6.7 | 6.5 |
| | 2 | 5.3 | 9.3 | 7.5 |
| | 1 | 7.5 | 11.5 | 7.5 |
| | 0.5 | 9.2 | 13.3 | 7.0 |
| DAG allyl ester | 8 | 2.5 | 3.0 | 3.5 |
| | 4 | 3.2 | 6.2 | 4.5 |
| | 2 | 5.0 | 10.0 | 5.0 |
| | 1 | 6.7 | 12.0 | 7.0 |
| | 0.5 | 8.8 | 13.0 | 7.0 |
| Maleic hydrazide | 4 | 5.8 | 6.3 | 4.0 |
| IT 3233 | 1 | 8.8 | 12.5 | 6.0 |
| IT 3456 | 1 | 8.7 | 9.8 | 5.5 |

TABLE II

Green Weight of Crabgrass Tops and Bluegrass Clipping after Post-Emergence Application of Growth Retardant Compounds

| Cpd | Rate, lbs./ Acre | Weight, grams, after days Since Application | |
|---|---|---|---|
| | | Crabgrass 18 days | Bluegrass 26 days |
| Untreated control | — | 18.9 | 4.6 |
| DAG | 8 | 4.4 | 2.7 |
| | 4 | 9.0 | 5.2 |
| | 2 | 14.0 | 5.7 |
| | 1 | 12.4 | 8.5 |
| | 0.5 | 20.8 | 4.4 |
| DAG methyl ester | 8 | 6.1 | 2.7 |
| | 4 | 13.0 | 5.3 |
| | 2 | 18.3 | 5.3 |
| | 1 | 19.3 | 5.7 |
| | 0.5 | 19.4 | 5.7 |
| DAG ethyl ester | 8 | 10.0 | 3.5 |
| | 4 | 13.5 | 5.3 |
| | 2 | 18.3 | 5.1 |
| | 1 | 19.3 | 4.2 |
| | 0.5 | 18.9 | 3.2 |
| DAG n-butyl ester | 8 | 6.2 | 3.0 |
| | 4 | 10.2 | 4.2 |
| | 2 | 17.9 | 4.3 |
| | 1 | 19.6 | 4.1 |
| | 0.5 | 21.1 | 4.8 |
| DAG allyl ester | 8 | 8.3 | 2.0 |
| | 4 | 14.9 | 4.0 |
| | 2 | 18.8 | 3.7 |
| | 1 | 20.1 | 3.3 |
| | 0.5 | 21.1 | 5.0 |
| Maleic hydrazide | 4 | 4.7 | 1.9 |
| IT 3233 | 1 | 10.4 | 4.4 |
| IT 3456 | 1 | 10.2 | 4.2 |

Of all the compounds evaluated, 2,3:4,6-di-O-isopropylidene-2-keto-L-gulonic acid (DAG) is the most active as a crabgrass retardant with the methyl, n-butyl and allyl esters almost as active. DAG is more active against crabgrass and bluegrass than the maleic hydrazide and morphactin standards at equivalent rates.

Since solvent solutions are not practical for field use and studies, tests of DAG and its derivatives were also carried out using emulsifiable formulations of the esters. (25% active ingredient, 71% xylene, 2% Atlox 3404, 2% Atlox 3403). Several esters were also evaluated in the aforedescribed solvent mixture. In addition, aqueous solutions of DAG containing 1% Tween 20 (polyoxysorbitan monostearate) either unbuffered or buffered at pHs 5–7 were prepared. Aqueous solutions of the salts of DAG also contained Tween 20.

Growth retarding evaluations were carried out on a plant spectrum of crabgrass, soybean and tomato with the plants sprayed with approximately two weeks old. When sprayed crabgrass was about 2 cm. tall, the soybean plants were 5–6 cm. tall with primary-leaves and the tomatoes were 3–4 cm. tall with 3–4 true leaves. Either water solutions, solvent mixtures or emulsifiable concentrates of the active ingredients were sprayed.

The results of these evaluations of DAG, its salts and esters in different formulations are listed in Table III wherein the retardant response rating is set forth numerically. The rating code is as follows:

TABLE III

Post-Emergence Herbicidal Activity of DAG and its Derivatives

| Compound | Form* | Rate lb./Acre | Retardant Response After 13 days | | |
|---|---|---|---|---|---|
| | | | Crabgrass | Soybean | Tomatoes |
| DAG | SM | 8 | 8 | 6.7 | 8 |
| | | 4 | 7 | 3 | 8 |
| | | 2 | 6 | 3 | 7.3 |
| | | 1 | 5 | 2 | 5 |
| | | 0.5 | 4.3 | 1 | 1.1 |
| DAG | Water | 8 | 9 | 9 | 10 |
| | | 4 | 9 | 8 | 9.7 |
| | | 2 | 8 | 7 | 9 |
| | | 1 | 6 | 6.7 | 8.7 |
| | | 0.5 | 5 | 6.7 | 8.3 |
| DAG | Water | 8 | 9 | 9 | 10 |
| | | 4 | 9 | 9 | 9 |
| | | 2 | 7.7 | 7.7 | 8.3 |
| | | 1 | 6.7 | 7 | 7 |
| | | 0.5 | 4 | 6 | 8 |
| DAG sodium salt | Water | 8 | 8.3 | 9 | 9 |
| | | 4 | 9 | 8 | 8 |
| | | 2 | 7 | 6.3 | 5.7 |
| | | 1 | 4 | 3.7 | 6.3 |
| | | 0.5 | 3 | 0 | 3 |
| DAG potassium salt | Water | 8 | 9 | 9 | 8 |
| | | 4 | 9 | 8 | 7.7 |
| | | 2 | 7.3 | 7.3 | 6.7 |
| | | 1 | 5 | 3 | 4.7 |
| | | 0.5 | 2 | 0 | 5 |
| DAG Ammonium salt | Water | 8 | 9 | 9 | 9 |
| | | 4 | 9 | 7.7 | 8 |
| | | 2 | 8 | 6.7 | 6 |
| | | 1 | 4 | 3.3 | 5 |
| | | 0.5 | 4 | 2 | 5 |
| DAG, Calcium salt | Water | 8 | 9 | 9 | 9 |
| | | 4 | 8 | 8 | 9 |
| | | 2 | 8 | 7.3 | 6 |
| | | 1 | 4.7 | 3 | 5 |
| | | 0.5 | 3.7 | 1 | 5 |
| DAG Methyl ester | SM | 8 | 9 | 9 | 7.7 |
| | | 4 | 8 | 3 | 5 |
| | | 2 | 4 | 1 | 3.3 |
| | | 1 | 3 | 0 | 0 |
| | | 0.5 | 0 | 0 | 0 |
| DAG n-butyl ester | SM | 8 | 9 | 6 | 7 |
| | | 4 | 8 | 6 | 6.7 |
| | | 2 | 7 | 3 | 5 |
| | | 1 | 5 | 1.3 | 5 |
| | | 0.5 | 4 | 0 | 0 |
| DAG n-butyl ester | EC | 8 | 10 | 9 | 8 |
| | | 4 | 9.3 | 9 | 7.3 |
| | | 2 | 7.7 | 8.3 | 8 |

TABLE III-continued

Post-Emergence Herbicidal Activity of DAG and its Derivatives

| Compound | Form* | Rate lb./Acre | Retardant Response After 13 days | | |
|---|---|---|---|---|---|
| | | | Crabgrass | Soybean | Tomatoes |
| | | 1 | 5.7 | 7 | 8 |
| | | 0.5 | 3.7 | 5 | 3 |
| Maleic hydrazide | Water | 8 | 7 | 10 | 5.7 |
| | | 4 | 7 | 10 | 3 |
| | | 2 | 5 | 9 | 1 |
| | | 1 | 0 | 9 | 0 |
| | | 0.5 | 0 | 9 | 0 |
| IT 3456 | SM | 8 | 5.7 | 8 | 5 |
| | | 4 | 5 | 8 | 5 |
| | | 2 | 3 | 8 | 5 |
| | | 1 | 0 | 8 | 5 |
| | | 0.5 | 0 | 8 | 5 |
| DAG allyl ester | SM | 8 | 8.3 | 8 | 9 |
| | | 4 | 7.3 | 8 | 8.3 |
| | | 2 | 5.3 | 7.3 | 5 |
| | | 1 | 4 | 1.3 | 1 |
| | | 0.5 | 2.7 | 0 | 0 |
| DAG n-dodecyl ester | SM | 8 | 8 | 5 | 8 |
| | | 4 | 7 | 3 | 7 |
| | | 2 | 4 | 3 | 6.3 |
| | | 1 | 2 | 2 | 2.3 |
| | | 0.5 | 2 | 2 | 2 |
| DAG n-dodecyl ester | EC | 8 | 8.7 | 8.3 | 6.3 |
| | | 4 | 8 | 6.3 | 4.3 |
| | | 2 | 3 | 5 | 4.3 |
| | | 1 | 3 | 5 | 4 |
| | | 0.5 | 0 | 5 | 3 |
| Control | EC | — | — | 9 | 8.3 |

*SM - solvent solution
ec - emulsifiable concentrate
Water -
(a) for salts of DAG, the water contained 1% Tween
(b) for DAG, the pH of the water was adjusted to 5 and 1% Tween plus 10% isopropyl alcohol were added.
0 - no visible retardation
1, 2, 3 - slight retardation, plants have little or no reduction in top growth
4, 5, 6 - moderate retardation, plants have reduced top growth
7, 8, 9 - severe retardation, plants have little to no growth
10 - no growth.

The activity of DAG in aqueous solutions was enhanced by buffering to a pH of from 5–7, an effect attributable to DAG's increased stability at this pH range. This enhanced effect was greater on soybean and tomato plants than on crabgrass. The inorganic salts and the ester derivatives of DAG were almost as active as DAG itself. The data show that DAG, its salts and its esters are more active than the maleic hydrazide and morphactin IT 3456 standards as post-emergence crabgrass growth retardant and slightly less active as a post-emergence soybean growth retardant.

The following Table IV lists data on a plant spectrum of 12 crops and weeds with the plants sprayed when approximately two weeks old. Four representative esters of DAG (2,3:4,6-di-O-isopropylidene-2-keto-L-gulonic acid) were compared to a standard, maleic hydrazide. The same rating scale as in Table III was used.

On tomato plants the terminal growth points are strongly retarded. There is, instead, a stimulation of lateral bud development with the resulting production of a dwarfed, bushy plant. There is not, however, any loss in either fruit quality or quantity.

TABLE IV

Post-Emergence Growth Retardant Effect of 2,3:4,6-di-0-isopropylidene-2-keto-L-Gulonic Acid (DAG) and its Derivatives

| Cpd | Formulation | Rate, lbs./Acre | Days | Barnyard Grass | Corn | Crabgrass | Johnson Grass | Kentucky Blue Grass | Oats | Rice | Soy-Bean | Sugar Beet | Tomato | Wheat | Wild Oats |
|---|---|---|---|---|---|---|---|---|---|---|---|---|---|---|---|

TABLE IV-continued

| | | | | | | | | | | | | | | | | |
|---|---|---|---|---|---|---|---|---|---|---|---|---|---|---|---|---|
| DAG Methyl ester | Solvent Mixture | 8 | 13 | 5 | 6 | 8 | 7 | 9 | 5 | 7 | 8 | 3 | 0 | 5 | 5 |
| | | 4 | | 4 | 5 | 5 | 6 | 8 | 5 | 5 | 7 | 0 | 0 | 3 | 4 |
| | | 2 | | 2 | 4 | 3 | 5 | 7 | 3 | 3 | 2 | 0 | 0 | 3 | 2 |
| | | 1 | | 0 | 0 | 2 | 2 | 6 | 0 | 0 | 0 | 0 | 0 | 0 | 0 |
| | | 0.5 | | 0 | 0 | 0 | 0 | 2 | 0 | 0 | 0 | 0 | 0 | 0 | 0 |
| DAG Ethyl ester | Solvent Mixture | 8 | 13 | 5 | 5 | 7 | 5 | 8 | 5 | 3 | 6 | 4 | 4 | 4 | 3 |
| | | 4 | | 2 | 2 | 6 | 3 | 7 | 2 | 2 | 3 | 2 | 4 | 0 | 0 |
| | | 2 | | 0 | 0 | 3 | 2 | 3 | 0 | 0 | 0 | 0 | 0 | 0 | 0 |
| | | 1 | | 0 | 0 | 0 | 0 | 0 | 0 | 0 | 0 | 0 | 0 | 0 | 0 |
| | | 0.5 | | 0 | 0 | 0 | 0 | 0 | 0 | 0 | 0 | 0 | 0 | 0 | 0 |
| DAG n-butyl ester | Solvent Mixture | 8 | 13 | 6 | 6 | 8 | 8 | 9 | 4 | 6 | 9 | 5 | 5 | 5 | 4 |
| | | 4 | | 5 | 0 | 7 | 7 | 9 | 3 | 5 | 8 | 3 | 4 | 3 | 3 |
| | | 2 | | 4 | 0 | 7 | 6 | 8 | 0 | 3 | 3 | 1 | 3 | 2 | 2 |
| | | 1 | | 2 | 0 | 5 | 2 | 7 | 0 | 2 | 2 | 0 | 0 | 0 | 0 |
| | | 0.5 | | 0 | 0 | 0 | 0 | 0 | 0 | 0 | 0 | 0 | 0 | 0 | 0 |
| Maleic hydrazide | Water | 8 | 13 | 4 | 0 | 7 | 7 | 9 | 3 | 5 | 8 | 3 | 7 | 2 | 3 |
| | | 4 | | 4 | 0 | 7 | 7 | 8 | 2 | 4 | 7 | 0 | 6 | 2 | 2 |
| | | 2 | | 3 | 0 | 3 | 4 | 7 | 0 | 3 | 6 | 0 | 6 | 2 | 2 |
| | | 1 | | 2 | 0 | 2 | 2 | 7 | 0 | 0 | 2 | 0 | 0 | 2 | 0 |
| | | 0.5 | | 0 | 0 | 0 | 0 | 2 | 0 | 0 | 0 | 0 | 0 | 0 | 0 |
| DAG n-propyl ester | Solvent Mixture | 8 | 14 | 8 | — | 7 | 7 | — | — | — | — | — | — | — | 7 |

| | | Post-Emergence Growth Retardant Effect of DAG Derivatives | | | | |
|---|---|---|---|---|---|---|
| Cpd | Form | Rate lbs./Acre | Days | Barn-yard Grass | John-son Grass | Crab Grass |
| DAG dimethyl ammonium salt | Water | 8 | 21 | 8 | 7 | 10 |
| | | 8 | 14 | 8 | 9 | 10 |
| | | 4 | 13 | 7 | 5 | 9 |
| | | 2 | 13 | 5 | 3 | 8 |
| | | 1 | 13 | 4 | 2 | 7 |
| DAG n-pentyl ester | SM | 8 | 14 | 10 | 9 | 10 |
| | | 4 | 13 | 7 | 7 | 9 |
| | | 2 | 13 | 5 | 5 | 8 |
| | | 1 | 13 | 2 | 5 | 7 |
| DAG isopropyl ester | SM | 8 | 14 | 7 | 8 | 8 |
| DAG Benzyl ester | SM | 8 | 14 | 8 | 8 | 9 |
| | | 4 | 13 | 7 | 7 | 9 |
| | | 2 | 13 | 5 | 6 | 8 |
| | | 1 | 13 | 3 | 5 | 8 |
| DAG n-ethanol ammonium salt | Water | 8 | 14 | 9 | 9 | 9 |
| | | 4 | 13 | 7 | 7 | 9 |
| | | 2 | 13 | 5 | 6 | 8 |
| | | 1 | 13 | 4 | 5 | 7 |

"Water" and "SM" have the same connotation as in Table III.

In tables III–IV the application rates of the salts, esters and other analogs of DAG were not adjusted for acid equivalency.

While primarily of use as a post-emergent growth regulant, the active compounds of this invention can also demonstrate utility as pre-emergent materials. For example, the pre-emergence herbicidal activity of DAG compounds is demonstrated by the n-propyl ester of DAG. The ester was applied by spraying at an 8 lbs./acre rate. Severe retardation (i.e., little to no growth) for Johnson grass, pigweed and crabgrass after 20 and 27 days was shown.

Additional evaluations of DAG and its salts were made with a variety of grasses, cereals, ornamental plants, woody perennials and vegetables.

Growth retardant studies on a variety of grasses were made using an emulsifiable concentrate of DAG in nitropyrrolidone. All species but Lolium were sprayed 4 days after cutting. Lolium (perennial ryegrass) was cut and sprayed on the same day.

Plant response, i.e., growth retardation is determined by grass height measurements made 19 or 21 days after spray application.

Maleic hydrazide (MH) and Chlorflurecol (CF) were used as reference standards.

Results are listed in the following Table V.

TABLE V

| Post-Emergent Retardant Activity | | | | | |
|---|---|---|---|---|---|
| A. Growth retardation after 19 days Grass Height, cm | | | | | |
| Cpd. Application Rate, kg a.i./ha | DAG 12 | DAG 18 | DAG 24 | MH 3 | Untreated Control — |
| Grass Species | | | | | |
| Agropyron repens | 7.2 | 6.3 | 5.3 | 10.7 | 14.7 |
| Bromus inermis | 10.2 | 8.2 | 7.3 | 12.3 | 14.3 |
| Bromus erectus | 8.5 | 7.7 | 7.7 | 9.5 | 12.0 |
| Deschampsia flexuosa | 3.2 | 3.4 | 3.4 | 3.3 | 3.6 |
| Alopecurus practensis | 10.3 | 9.7 | 7.7 | 14.3 | 17.0 |
| Arrhenatherum elatius | 7.8 | 7.3 | 6.8 | 11.7 | 16.7 |
| Dactylis glomerata | 11.7 | 10.8 | 9.7 | 13.3 | 18.0 |
| Festuca pratensis | 9.5 | 8.5 | 7.7 | 12.0 | 14.3 |
| Trisetum flavescens | 9.0 | 8.5 | 9.7 | 11.7 | 38.0 |

TABLE V-continued

Post-Emergent Retardant Activity

| | | | | | |
|---|---|---|---|---|---|
| Holcus lanatus | 8.0 | 7.7 | 7.8 | 10.5 | 14.3 |
| Lolium perenne | 14.3 | 12.7 | 13.3 | 13.3 | 18.7 |

B. Growth Retardation after 21 days
Grass Height, cm

| Cpd. | DAG | DAG | DAG | CF | Untreated Control |
|---|---|---|---|---|---|
| Application Rate, kg a.i./ha | 4 | 8 | 16 | 1 | — |
| Grass Species | | | | | |
| Poa annua | 8.7 | 7.3 | 7.0 | 7.5 | 8.7 |
| Poa nemoralis | 18.3 | 6.8 | 7.2 | 8.7 | 22.3 |
| Festuca ovina | 14.0 | 7.5 | 9.3 | 9.0 | 15.0 |
| Festuca rubra | 18.3 | 13.3 | 12.8 | 11.7 | 18.7 |
| Festuca nigrescens | 13.0 | 8.5 | 8.3 | 10.5 | 12.8 |
| Cynosurus cristatus | 10.7 | 6.8 | 7.0 | 9.5 | 12.0 |
| Agrostis schraderiana | 6.7 | 4.7 | 5.0 | 5.3 | 7.7 |
| Agrostis stolonifera | 6.7 | 4.0 | 4.0 | 5.2 | 6.7 |
| Phleum pratense | 11.7 | 11.0 | 10.7 | 10.8 | 12.3 |
| Phleum nodosum | 7.3 | 6.5 | 7.0 | 7.0 | 8.2 |
| Cynodon dactylon | 10.8 | 7.3 | 7.3 | 7.0 | 10.7 |

Table VI shows the effect of DAG and its sodium salt on barley and wheat. Height was measured 41 days after spraying.

TABLE VI

| | | | Plant height, cm, 41 days after Spraying | | | |
|---|---|---|---|---|---|---|
| | | | Barley | | Wheat | |
| | Plant Age at Treatment, days | | 28 | 10 | 28 | 10 |
| Cpd | Formulation | Application Rate, kg a.i./ha | | | | |
| DAG | Emulsifiable concentrate | 6 | 51.5 | 41.5 | 62.8 | 42.5 |
| | Emulsifiable concentrate | 12 | 48.4 | 47.1 | 58.5 | 40.5 |
| DAG sodium salt | Water | 6 | 43.4 | 43.4 | 46.6 | 37.5 |
| | Water | 12 | 32.9 | 33.9 | 33.6 | 25.0 |
| Untreated Control | | — | 48.6 | 47.6 | 61.3 | 43.4 |

The effect of DAG, in an emulsifiable concentrate, in nitropyrrolidone, on two hedge species is shown in Table VII. In the case of carpinus betulus (hornbeam), visual observations made 2 months after the evaluation in Table VII indicated greater growth retardation than reported in the table. The amount of active ingredient in the solvent is reported as percentages in the Table.

TABLE VII

| | Hedge height, cm, 34 days after Spraying | |
|---|---|---|
| Compound | Thuja fastigiata occidentalis (Northern White Cedar) | Carpinus betulus (Hornbeam) |
| Untreated Control | 70 | 52 |
| DAG, 0.5% | 33 | 48 |
| DAG, 1.0% | 25 | 15 |
| DAG, 2.0% | 18 | 48 |

The effect of DAG on apples and vines in comparison to two reference standards, CCC and Alar, is shown in Table VIII.

TABLE VIII

| | | Height, cm, for weeks after Application | |
|---|---|---|---|
| Compound | Application Rate, % a.i. | 11 weeks Apple | 9 weeks Vine |
| Untreated control | — | 25.4 | 21.4 |
| DAG | 0.1 | 25.7 | 16.5 |
| DAG | 0.2 | 17.7 | 13.2 |
| DAG | 0.4 | 9.8 | 15.0 |
| CCC | 0.2 | 23.2 | 24.5 |
| Alar | 0.2 | 31.2 | 26.0 |

DAG's effect on geranium in comparion to CCC reference standard is shown in Table IX.

TABLE IX

| | Height, cm, four weeks after Spraying | |
|---|---|---|
| Concentration a.i. p.p.m. | DAG | CCC |
| 8000 | 16.0 | 13.6 |
| 4000 | 14.2 | 13.0 |
| 2000 | 15.7 | 14.3 |
| 1000 | 15.9 | 14.4 |
| 500 | 17.1 | 17.2 |
| 250 | 19.4 | 16.6 |
| Untreated Control | 20.0 | |

Growth retardation on Chrysanthemum morifolium of DAG and Alar reference standard is shown in Table X. The initials "a.i." mean "active ingredient".

TABLE X

| Compound | Application Rate, p.p.m. | Average length, cm, of side shoots four weeks after spraying |
|---|---|---|
| DAG | 3000 | 16.6 |
| | 2000 | 17.8 |
| | 1000 | 19.3 |
| | 500 | 17.9 |
| | 250 | 18.0 |
| Alar | 4000 (a.i.) | 17.3 |
| Untreated Control | — | 20.9 |

Table XI shows the effect of DAG and Ethrel reference standard on tomatoes as to both plant height and number of flowers.

TABLE XI

| | | Age of plants at spraying, days | |
|---|---|---|---|
| Compound | Application rate, ppm | 32 | 60 |
| | | Height, cm, of tomato plants 30 days after spraying | |
| DAG | 1000 | 25.7 | 52.3 |
| | 4000 | 17.3 | 34.0 |
| Ethrel | 1000 (a.i.) | 27.0 | 54.3 |
| | 4000 (a.i.) | 15.0 | 27.3 |
| Untreated Control | — | 34.3 | 56.7 |
| | | Number of flowers 30 days after spraying | |
| DAG | 1000 | 6.3 | 20.0 |
| | 4000 | 2.3 | 8.7 |
| Ethrel | 1000 (a.i.) | 3.7 | 15.0 |
| | 4000 (a.i.) | 3.0 | 0 |
| Untreated Control | — | 6.8 | 5.0 |

DAG, its ammonium salt and its n-butyl ester were evaluated as growth retardants for woody perennials, Brazilian pepper (*Schinus terebinthifolius* Raddi) and sumac (*Rhus* spp.). Application was by foliage spray to run off. Maintain CF-125 was used as the reference standard. Forty-three days after spray application, observations were made as to stunting and killing of terminal growth, defoliation and deformity of leaves. In Table XII, the retardation response rating is set forth numerically. The rating code is as follows:

TABLE XII

| Cpd | Concentration in Spray, % | Growth Regulant Effect on Brazilian Pepper and Sumac 43 Days after Application | |
|---|---|---|---|
| | | Brazilian pepper | Sumac |
| Untreated Control | — | 0 | 0 |
| DAG | 0.25 + 2% oil | 0 | 0 |
| DAG | 0.5 + 2% oil | 0 | 1 |
| DAG | 1.0 + 2% oil | 1 | 2 |
| DAG | 1.0 | 0 | 2 |
| DAG ammonium salt | 0.25 + 1% Triton® B-1956® | 0 | 1 |
| DAG ammonium salt | 0.5 + 1% Triton® B-1956® | 1 | 2 |
| DAG ammonium salt | 1.0 + 1% Triton® B-1956® | 2 | 2 |
| DAG n-butyl ester | 0.25 + 2% oil | 0 | 0 |
| | 0.5 + 2% oil | 0 | 2 |
| | 1.0 + 2% oil | 1 | 2 |
| | 1.0 | 0 | 2 |
| Maintain CF-125 | 0.5 | 3 | 4 |

0 - No effect
1 - Terminal growth stunted
2 - Terminal growth killed
3 - Terminal growth killed, leaves deformed
4 - Complete leaf drop, new leaves small and deformed.
Triton® B-1956® - a water-dispersible, resin-based surfactant manufactured by Rohm and Haas.
Maintain CF-125 is a mixture of methyl-2-chloro-9-hydroxyfluorene-9-carboxylate, methyl-9-hydroxy-fluorine-9-carboxylate and methyl-2,7-dichloro-9-hydroxyfluorene-9-carboxylate.

The oil adjuvant used in the above formulations is the standard type petroleum oil commonly used with herbicide formulations for application to woody plants. If functions to both aid penetration and sticking of the active compounds. Sun Oil 11E, an emulsifiable, non-phytotoxic spray oil was used in the formulations of Table XII.

The herbicidal activity of DAG both alone and in combination with 2,4-D, is demonstrated in spray applications against a variety of species. Table XIII shows the effect of spray application of a DAG emulsifiable concentrate in nitropyrrolidone. Data is reported as percent control relative to the untreated species.

TABLE XIII

| | % Control 16 days after Spraying | | | |
|---|---|---|---|---|
| Rate, kg a.i./ha Species | DAG 4 | DAG + 2,4-D 4 + 0.5 | CMPP + 2,4-D 1.5 + 0.5 | MCPA + CMPP + Ioxynil 0.25 + 0.8 + 0.3 |
| *Chrysanthamum segetum* | 65 | 65 | 5 | 45 |
| *Matricaria chamomilla* | 85 | 90 | 15 | 55 |
| *Convolvulus arvensis* | 0 | 70 | 85 | 90 |
| *Galium aparina* | 0 | 45 | 85 | 75 |
| *Sinapis arvensis* | 0 | 70 | 90 | 95 |
| *Daucus carota* | 0 | 85 | 90 | 100 |
| *Rumex obtusifolius* | 30 | 60 | 85 | 90 |
| *Papaver rhoeas* | 75 | 90 | 65 | 90 |
| *Galeopsis tetrahit* | 50 | 40 | 40 | 60 |

The herbicidal activity of DAG, either alone or in combination with 2,4-D, was evaluated on Daucus carota (wild carrots) using spray application of an emulsifiable concentrate in nitropyrrolidone. Table XIV records the % epinasty 4 and 18 days after spraying. (Epinasty is the nastic movement by which a plant part is bent outward and often downward.) These results indicate that DAG enhances the activity of 2,4-D.

TABLE XIV

| Cpd Rate, | % Epinasty | |
|---|---|---|
| kg a.i./ha | After 4 days | After 18 days |
| Untreated Control | 0 | 0 |
| DAG - 8 | 0 | 0 |
| 2,4-D(Na) - 1 | 15 | 50 |
| DAG + 2,4-D | | |
| 8 + 1 | 80 | 95 |
| 8 + 0.5 | 80 | 80 |
| 4 + 1 | 90 | 90 |

The preferred active growth retardant and herbicidal compounds of this invention are, thus, 2,3:4,6-di-O-isopropylidene-2-keto-L-gulonic acid (DAG), its sodium, potassium, ammonium, calcium and dimethyl ammonium salts and its lower alkyl and lower alkenyl esters.

2,3:4,6-di-O-isopropylidene-2-keto-L-gulonic acid monohydrate is a well-known chemical of commerce and is an intermediate in the formation of L-ascorbic acid. It is prepared by the oxidation in alkaline or neutral media of diacetone-L-sorbofuranose which is, in turn, prepared from the reaction of L-sorbose with acetone in the presence of a strong acid. This procedure is described in detail in U.S. Pat. No. 2,301,811, issued Nov. 10, 1942 to Reichstein. An alternative method of preparation is described in U.S. Pat. No. 3,832,355, issued Aug. 27, 1974 to Jaffe et al.

Salts of DAG are prepared by conventional processes. DAG is added with rapid stirring to an aqueous solution of a base at room temperature. The solution is monitored to maintain pH above 7. Upon completion of the reaction, excess water is removed under high vacuum. Anhydrous acetone is then added to the resulting syrup (about 10 volumes) with overnight stirring. The white crystalline precipitate which forms is filtered, washed with acetone and dried. In the case of the non-volatile bases, e.g. NH$_4$OH and (CH$_3$)$_2$NH, excess base is added and the excess is subsequently removed in the vacuum evaporation.

Since DAG is not stable under normal esterification conditions such as the Fischer esterification procedure, the novel esters of DAG are prepared by reaction with the appropriate lower alkyl, lower alkenyl or lower alkinyl halide under basic conditions at room temperature using an inert organic solvent such as dimethyl formamide (DMF). The esters are insoluble in water but soluble in methanol, acetone, ethanol, chloroform, pentane, benzene, ether and the like.

Solvent solutions of the compounds, while suitable for greenhouse evaluations, are not amenable for field applications. Wettable powders used directly were also found to be unsatisfactory since DAG derivatives must be solubilized in order to be active. The acid is preferably prepared as a soluble powder with buffering agents since buffering to pH 5-9 is essential for the acid.

The acid may also be prepared as an emulsion concentrate using N-methyl-2-pyrrolidone or nitropyrrolidone according to the following formulation:

| | % by weight of Total Composition |
|---|---|
| DAG | 50 |
| Atlox 2081B | 4 |
| N-methyl-2-pyrrolidone or | |
| Nitropyrrolidone | 46 |

Atlox 2081B is a blend of polyoxyethylene sorbitan esters of fatty and resin acids and alkyl aryl sulfonate.

The salts are, of course, water-soluble and need no special formulation.

The DAG esters are formulated as xylene-based emulsifiable concentrates for mixing with water. Emulsions are prepared from these concentrates which contain from 25% to 50% by weight of the active ingredient. Typical emulsifiable concentrates for the DAG esters are listed below.

| | % by weight of Total Composition | |
|---|---|---|
| Active Ingredient | 25 | 50 |
| Xylene | 71 | 46 |
| Atlox 3403 | 2 | — |
| Atlox 3404 | 2 | — |
| Emulphor EL 620 | — | 2 |
| Drewmulse GMC-8 | — | 2 |

Atlox 3403 is a blend of polyoxyethylene ethers, polyoxyethylene glyceride and an alkyl aryl sulfonate.
Atlox 3404 is a blend of polyoxyethylene alkyl aryl ether and an alkyl aryl sulfonate.
Emulphor EL 620 is a polyethylated vegetable oil.
Drewmulse GMC-8 is a monoglyceride of low molecular weight saturated coconut fatty acid.

A dry wettable powder composition is prepared by admixing the following ingredients, in percents by weight based on the total weight of the composition:

| Ingredient | % |
|---|---|
| Sodium salt of 2,3-di-0-isopropylidene-2-keto-L-gulonic acid | 90.0 |
| Duponol ME Dry[1] | 6.0 |
| Sodium stearate (antifoaming agent) | 0.5 |
| Aerosil R-972[2] | 2.5 |
| Sodium carbonate, anhydrous | 1.0 |

[1] Duponol ME Dry (DuPont) is sodium lauryl sulfate.
[2] Aerosil R-972 (Degussa) is a silicagel anticaking agent.

This formulation corresponds to one having an anhydrous acid equivalent of 80% 2,3:4,6-di-O-isopropylidene-2-keto-L-gulonic acid.

This composition is added to water to form solutions which contain an amount of the active ingredient effective for plant growth regulation when used as a spray.

B. Evaluation of additional compounds analogous to 2,3:4,6-di-O-isopropylidene-2-keto-L-gulonic acid These compounds, in which $R_1$ and $R_{2b}$ or $R_1$, $R_2$, $R_3$ and $R_4$ of Formula I are other than methyl, also show both pre- and post-emergent growth regulant activity. For example, 2,3:4,6-di-O-cyclohexylidene-2-keto-L-gulonic acid, applied at the rate of 8 lbs./acre as a pre-emergent growth retardant completely inhibits growth of pigweed even 20 days after application and as a post-emergent growth regulant causes severe retardation of red kidney bean growth. 2,3:4,6-di-O-(3-pentylidene)-2-keto-L-gulonic acid, applied at the rate of 8 lbs./acre, as a post-emergent growth regulant causes severe retardation of pigweed, mustard, morning glory and red kidney bean.

Compounds in which the 4,6-O-isopropylidene group has been replaced are prepared by a ketal interchange reaction in which DAG is dissolved in the desired ketone, aldehyde, ketal or acetal using an acid catalyst.

Representative of the ketones and aldehydes which can be used in the preparatory procedure are those of the general formula

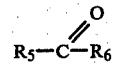

wherein $R_5$ can be, e.g. methyl, ethyl, lower alkyl phenyl or p-methoxyphenyl and $R_6$ can be, e.g. methyl, ethyl, loweralkyl or hydrogen. Typical compounds include diethyl ketone, methyl ethyl ketone, paraldehyde, benzaldehyde, and p-methoxyaldehyde. Ketones in which both R groups are large are not satisfactory due to possible steric hindrance effects. Where an unsymmetrical aldehyde or ketone is used, the larger or bulkier group occupies the "exo" position ($R_1$ of Formula I) to form a new asymmetric center.

Any strong acid can be used as the catalyst with perchloric acid the preferred catalyst. Other representative acids include sulfuric acid, hydrochloric acid, p-toluene sulfonic acid, methane sulfonic acid and trifluoromethane sulfonic acid.

A temperature range of from about −20° C. to about 50° C. can be used with a range of 20° C.-30° C. (room temperature) preferred. 100° C., near the decomposition point of DAG, is the limiting temperature.

The compounds in which both O-isopropylidene groups have been replaced are prepared from L-sorbose following the procedure described in Reichstein and Grussner, Helv. Chim. Acta, 17, 311 (1934) and in U.S. Pat. No. 2,301,811, issued Nov. 10, 1942 to Reichstein. An alternative procedure is described in U.S. Pat. No. 3,832,355, issued Aug. 27, 1974 to Jaffe et al. In brief, a suitable ketone or aldehyde is reacted with L-sorbose in the presence of a strong acid catalyst, i.e., sulfuric acid, at room temperature or below. The intermediate which forms, 2,3:4,6-di-O-alkylidene-α-L-sorbofuranose, is subsequently oxidized in alkaline or neutral media.

In the preparation of the di-O-alkylidene sorbofuranose, the strong acid catalysts include sulfuric acid, perchloric acid, hydrochloric acid, p-toluene sulfonic acid and the like with sulfuric acid preferred.

Since the reaction is exothermic room temperature or below are used with the preferred temperature range being from about 0° C. to about −20° C.

In the subsequent preparation of the acid from the sorbofuranose intermediate, oxidation is carried out in alkaline or neutral media using such agents as $NaMnO_4$, $K_2Cr_2O_7$, $KMnO_4/KOH$ and $NaOCl/Ni^{2+}$ with the latter two preferred. In addition, the oxidation can also be achieved catalytically using palladium or platinum and oxygen.

A temperature range of from room temperature to 100° C. can be used with a range from about 50° C. to about 60° C. preferred.

2,3:4,6-di-O-methylene-2-keto-L-gulonic acid was prepared as described below following the procedure in the aforesaid *Helv. Chim. Acta* publication. A solution of 30 grams of sulfuric acid in 35 grams of water were added to a mixture of 50 grams of trioxane and 10 grams of L-sorbose. The resulting solution was heated to 80° C. and then cooled on an ice bath. 250 ml. of a saturated solution of potassium carbonate was added and a salt separated. The salt was filtered and washed with potassium carbonate and chloroform. These washings were added to the filtrate which was then extracted four times with chloroform. The chloroform extracted were dried over sodium sulfate to yield 4.8 grams of a yellow syrup which after vacuum distillation at 0.1 mm and 130°–135° C., yielded a solid. This solid was recrystallized from benzene to yield 1.5 grams of white crystals of 2,3:4,6-di-O-methylene-α-L-sorbofuranose.

This material was heated at 50°–60° C. for 4 hours with 1.2 grams of potassium hydroxide and 0.8 grams of potassium permanganate in 25 ml. of water. An additional 0.8 grams of potassium permanganate were added and the reaction was stirred without heating overnight. The mixture was extracted with cold methylene chloride which was evaporated to a residue. The residue was taken up in toluene, filtered and allowed to crystallize to yield 2,3:4,6-di-O-methylene-2-keto-L-gulonic acid, m.p. 124°–125° C.

By analogous procedures using ketones and aldehydes of the general formula

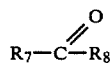

wherein $R_7$ can be halo-lower alkyl and $R_8$ can be halo-lower alkyl or hydrogen, active compounds in which $R_1$ and $R_2$ or $R_1$, $R_2$, $R_3$ and $R_4$ of Formula I are halo-lower alkyl can be prepared.

The following Examples illustrate the invention.

EXAMPLE 1

Ethyl ester of 2,3:4,6-di-O-isopropylidene-2-keto-L-gulonic acid

To a stirred suspension at room temperature of 100 g. of anhydrous potassium carbonate in 946 ml. of dimethylformamide were added 292.2 g. of 2,3:4,6-di-O-isopropylidene-2-keto-L-gulonic acid monohydrate (DAG monohydrate) followed by 205 g. of ethyl iodide. Stirring was continued for 24 hours at room temperature. The mixture was then filtered to remove any inorganic salts, dimethylformamide was removed by vacuum distillation (ca. 60° and ca. 10 mmHg) and 200 ml. of acetone were added to dissolve the ester residue. Any undissolved inorganic salts were removed by filtration. The resulting filter cake was washed with 100 ml. of acetone. This filtrate was combined with the ester solution and the crude product was isolated therefrom by vacuum reduction of the solvent to about 500 ml. and cooling to 5° C. The crude product was recrystallized from methanol or methanol-acetone to give 284 g. of ethyl-2,3:4,6-di-O-isopropylidene-2-keto-L-gulonate, m.p. 99°–100.5° C.

Analysis Calcd. for $C_{14}H_{22}O_7$ (%): C, 55.62; H, 7.34; $-OC_2H_5$, 14.91. Found (%): C, 55.94; H, 7.56; $-OC_2H_5$, 15.16.

IR ($CHCl_3$) bands at 3017, 1755, 1392 and 1400 cm$^{-1}$.

Following this general procedure using 2,3:4,6-di-O-isopropylidene-2-keto-L-gulonic acid and 1,2-dibromoethane in a 2:1 mol ratio, the bis ester: Bis-2,3:4,6-di-O-isopropylidene-2-keto-L-gulonate, ethylene glycol ester, is prepared.

EXAMPLE 2

Methyl-2,3:4,6-di-O-isopropylidene-2-keto-L-gulonate

To a stirred suspension of 100 g. of anhydrous potassium carbonate in 946 ml. of dimethylformamide was added 292.2 g. of 2,3:4,6-di-O-isopropylidene-2-keto-L-gulonic acid monohydrate (DAG monohydrate) and then 205 g. of methyl iodide. The mixture was stirred for four hours at room temperature and then filtered to remove any inorganic salts. Dimethylformamide was then removed by vacuum distillation.

200 Ml. of acetone were added to dissolve the ester residue. Undissolved inorganic salts were removed by filtration. The resulting filter cake was washed with 100 ml. of acetone. This filtrate was combined with the ester solution and concentrated under vacuum to a yellow syrup which crystallized to large prisms on standing. Vacuum distillation at 127°–129° at 0.35–0.37 mm yielded 268 grams of colorless liquid methyl-2,3:4,6-di-O-isopropylidene-2-keto-L-gulonate which solidified on standing, m.p. 46.5°–47.5° C.

Analysis Calcd. for $C_{13}H_{20}O_7$ (%): C, 54.16; H, 6.99. Found: C, 53.84; H, 7.06.

IR ($CHCl_3$) bands at 3000, 1755, 1380, 1390 cm$^{-1}$.

EXAMPLE 3 n-Butyl-2,3:4,6-di-O-isopropylidene-2-keto-L-gulonate

To a stirred suspension of 100 g. of anhydrous potassium carbonate in 946 ml. of dimethylformamide was added 292.2 g. of 2,3:4,6-di-O-isopropylidene-2-keto-L-gulonic acid monohydrate (DAG monohydrate) and then 197 g. of n-butyl iodide. The mixture was stirred for 48 hours at room temperature and then filtered to remove any inorganic salts. Dimethylformamide was removed by vacuum distillation. 200 Ml. of acetone were added to dissolve the ester residue. Any remaining inorganic salts were removed by filtration. The resulting filter cake was washed with 100 ml. of acetone. This filtrate was combined with the ester solution and concentrated under vacuum to the crude product. Recrystallization from methanol-acetone yielded 272 g. of colorless crystals, n-butyl-2,3:4,6-di-O-isopropylidene-2-keto-L-gulonate, m.p. 53.9°–56.8° C.

Analysis Calcd. for $C_{16}H_{26}O_7$ (%): C, 58.17; H, 7.93. Found (%): C, 58.06; H, 7.93.

IR (CHCl$_3$) bands at 2375-3025, 1740, 1368, 1375 cm$^{-1}$.

EXAMPLE 4 n-Propyl ester of 2,3:4,6-di-O-isopropylidene-2-keto-L-gulonic acid n-Propyl-2,3:4,6-di-O-isopropylidene-2-keto-L-gulonate is prepared by the procedure of Examples 1-3 above using 200 grams of 1-bromopropane as the halide. Yield was 150.6 grams, m.p. 80°-81° C.

EXAMPLE 5 n-Pentyl ester of 2,3:4,6-di-O-isopropylidene-2-keto-L-gulonic acid n-Pentyl-2,3:4,6-di-O-isopropylidene-2-keto-L-gulonate is prepared by the procedure of Examples 1-3 above using 300 grams of 1-bromopentane as the halide. Yield is 503 grams, b.p. 195° C. at ca. 0.1 mm.

Analysis Calcd. for C$_{17}$H$_{28}$O$_7$: C, 59.29; H, 8.20. Found: C, 59.15; H, 8.18.

EXAMPLE 6 n-Dodecyl ester of 2,3:4,6-di-O-isopropylidene-2-keto-L-gulonic acid n-Dodecyl-2,3:4,6-di-O-isopropylidene-2-keto-L-gulonate is prepared by the procedure of Examples 1-3 above using 100 grams of 1-bromododecane as the halide. Yield is 75 grams after two recrystallizations from ethanol, m.p. 10.5° C.

Analysis Calcd. for C$_{24}$H$_{46}$O$_7$: C, 64.54; H, 10.38. Found: C, 64.25; H, 10.50.

EXAMPLE 7

Allyl ester of 2,3:4,6-di-O-isopropylidene-2-keto-L-gulonic acid

Allyl-2,3:4,6-di-O-isopropylidene-2-keto-L-gulonate is prepared by the procedure of Examples 1-3 above using 133 grams of allyl bromide. Yield is 282 grams, m.p. 95°-95.5° C.

IR (CHCl$_3$) bands at 1757 cm$^{-1}$, 1379 cm$^{-1}$, 1385 cm$^{-1}$.

EXAMPLE 8

Benzyl ester of 2,3:4,6-di-O-isopropylidene-2-keto-L-gulonic acid

Benzyl-2,3:4,6-di-O-isopropylidene-2-keto-L-gulonate is prepared by the procedure of Examples 1-3 above using 100 grams of α-bromotoluene. Yield is 134.3 grams, m.p. 76°-77° C.

Analysis Calcd. for C$_{19}$H$_{24}$O$_7$: C, 62.63; H, 6.64. Found: C, 62.67; H, 6.65.

EXAMPLE 9

Isopropyl ester of 2,3:4,6-di-O-isopropylidene-2-keto-L-gulonic acid

Isopropyl-2,3:4,6-di-O-isopropylidene-2-keto-L-gulonate is prepared by the procedures of Examples 1-3 above using 250 grams of 2-bromopropane. Yield is 116.8 grams, m.p. 107.5°-109° C.

Analysis Calcd. for C$_{15}$H$_{24}$O$_7$: C, 56.95; H, 7.65. Found: C, 56.77; H, 7.70.

In a similar manner, other straight and branched chain hydrocarbyl and halo-lower alkyl esters can be prepared.

EXAMPLE 10

2,3-O-isopropylidene-4,6-O-ethylidene-2-keto-L-gulonic acid, sodium salt

48 Grams of 2,3:4,6-di-O-isopropylidene-2-keto-L-gulonic acid (DAG) were dissolved in 250 grams of paraldehyde. Five drops of 70% perchloric acid were added and the reaction was continued for 12 days at room temperature under monitoring by Thin Layer (TLC) or Gas Liquid Chromatography (GLC). This solution was then added with vigorous stirring to 16.8 grams of a sodium bicarbonate slurry in 100 ml. of water. Any excess paraledhyde and water were removed under vacuum. The residue was recrystallized from an alcohol/water mixture to yield 50.4 grams (89.4% of the sodium salt of 2,3-O-isopropylidene-4,6-O-ethylidene-2-keto-L-gulonic acid. Physical chemical data (n.m.r., Mass spectra, infrared) show the structure to be:

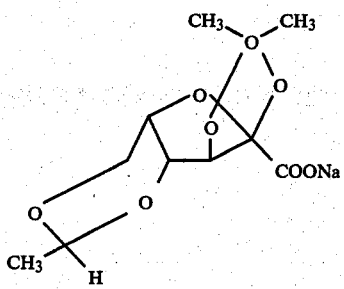

Analysis Calc'd for C$_{11}$H$_{15}$NaO$_7$(%): C, 46.81; H, 5.36; Na, 8.15. Found: C, 47.06; H, 5.26; Na, 8.18.

In like manner, other 2,3-O-isopropylidene-4,6-O-(R$_1$-R$_2$)-2-keto-L-gulonic acids, where the R$_1$ and R substituents are straight and branched chain aliphatic lower hydrocarbyl, halo-lower alkyl, aryl or R$_1$ and R$_2$ together, a saturated ring of from 3 to 8 carbon atoms can be prepared.

EXAMPLE 11

2,3-O-isopropylidene-4,6-O-(3-pentylidene)-2-keto-L-gulonic acid 29.2 Grams of DAG were dissolved in 500 ml of diethyl ketone. Five drops of 70% perchloric acid were added and the reaction was continued for 72 hours at room temperature. Yield of crude product was 30.3 grams. Purification by recrystallization from chloroform/hexane gave white platelets m.p. 129.8°-130.2° C. Physical Chemical data supported the proposed structure.

Analysis Calc'd for C$_{14}$H$_{22}$O$_7$: C, 55.62; H, 7.34. Found: C, 55.85; H, 7.50.

EXAMPLE 12

2,3-O-isopropylidene-4,6-O-benzylidene-2-keto-L-gulonic acid, sodium salt 58.4 Grams of DAG were dissolved in a mixture of 200 ml. of benzaldehyde and 200 ml. of methylene chloride. Methylene chloride is used to dissolve the DAG which was not completely soluble in the amount of benzaldehyde used. Three drops of 70% perchloric acid were added and the reaction was continued for 72 hours at room temperature. The solution was then added with vigorous stirring to a sodium bicarbonate-water slurry. Excess benzaldehyde, methylene chloride and water were removed under vacuum. The residue was recrystallized from an alcohol/water mixture to yield 37.0 grams (54%) of the sodium salt of 2,3-O-isopropylidene-4,6-O-benzylidene-2-keto-L-gulonic acid.

Analysis Calc'd. for $C_{16}H_{17}NaO_7$: C, 55.82, H, 4.98; Na 6.68. Found: C, 55.58; H, 5.18; Na 6.33.

EXAMPLE 13

2,3-O-isopropylidene-4,6-O-(p-methoxybenzylidene)-2-keto-L-gulonic acid, sodium salt 50 Grams of DAG were dissolved in 300 ml of p-methoxybenzaldehyde and 5 drops of 70% perchloric acid were added. The reaction was continued for 72 hours at room temperature. The solution was then added with vigorous stirring to a sodium bicarbonate-water slurry. Excess p-methoxybenzaldehyde and water were removed under vacuum. The residue was recrystallized from 95% ethanol to yield 46 grams of the sodium salt of 2,3-O-isopropylidene-4,6-O-(p-methoxybenzylidene)-2-keto-L-gulonic acid.

Analysis Calc'd for $C_{17}H_{19}NaO_8.H_2O$: C, 52.03; H, 5.40; Na, 5.86. Found: C, 51.90; H, 5.47; Na, 5.50.

EXAMPLE 14

2,3-O-isopropylidene-4,6-O-(2-butylidene)-2-keto-L-gulonic acid 29.2 Grams of DAG were dissolved in 500 ml. of methyl ethyl ketone and 5 drops of 70% perchloric acid were added thereto. The reaction was continued for 72 hours at room temperature. Yield of crude product was 57.6 grams. Purification by recrystallization from chloroform/hexane gave the free acid.

Analysis Calc'd for $C_{13}H_{20}O_7$: C, 50.97 H, 7.24 $H_2O$, 5.88. Found: C, 51.09 H, 7.46 $H_2O$, 6.20.

EXAMPLE 15

2,3:4,6-di-O-(3-pentylidene)-2-keto-L-gulonic acid

To 495 ml. of diethylketone cooled to 0° C. were added dropwise 81 grams of sulfuric acid followed by 120 grams of L-sorbose. The reaction was continued for 2 days with stirring at −10° to −20° C. The mixture was then neutralized with 600 ml. at 10% NaOH and the excess diethyl ketone was removed by vacuum distillation 2,3:4,6-di-O-(3-pentylidene)-α-L-sorbofuranose was isolated by extraction with toluene.

31.6 Grams of this intermediate, recrystallized from pentane, was heated for 4 hours at 50°–60° C. with 23.8 grams of potassium hydroxide and 15.8 grams of potassium permanganate in 250 ml. of water. An additional 15.8 grams of potassium permanganate were added and the reaction was stirred without heat overnight. The mixture was then filtered, concentrated to about 150 ml, cooled to −5° C. and then acidified to pH 3.0 with concentrated HCl. The resulting precipitate was filtered and washed with water. 26.8 Grams of product, m.p. 144°–145° C., were isolated by recrystallization. Physical chemical data supported the assigned structure.

Analysis Calc'd for $C_{16}H_{26}O_7$: C, 58.17; H, 7.93. Found: C, 58.11; H, 7.99.

In like manner other gulonic acid derivatives are prepared wherein $R_1$, $R_2$, $R_3$ and $R_4$ are hydrogen, straight or branched chain aliphatic lower hydrocarbyl, halo-lower alkyl or aryl.

EXAMPLE 16

2,3:4,6-di-O-(2-butylidene)-2-keto-L-gulonic acid, hydrate 2,3:4,6-di-O-(2-butylidene)-2-keto-L-gulonic acid, hydrate is prepared by the procedure described in Example 15 above using methyl ethyl ketone. The product, recrystallized from hexane/chloroform, has a melting point of 96.5°–103° C.

Analysis Calc'd or $C_{14}H_{22}O_7.H_2O$: C, 52.49; H, 7.55. Found: C, 52.50; H, 7.56.

EXAMPLE 17

2,3:4,6-di-O-cyclohexylidene-2-keto-L-gulonic acid 2,3:4,6-di-O-cyclohexylidene-2-keto-L-gulonic acid is prepared by the procedure described in Example 15 above using cyclohexanone. The product, recrystallized from hexane/acetone had a melting point of 125°–128.5° C.

In like manner other gulonic acid derivatives are prepared where $R_1$ and $R_2$ together and $R_3$ and $R_4$ together are saturated rings of from 3 to 8 carbon atoms.

EXAMPLE 18

Compositions, suitable for use in combination in spray application, were prepared by admixing the following ingredients:

| Composition A | |
|---|---|
| Ingredient | grams/liter |
| 2,3:4,6-di-0-isopropylidene-2-keto-L-gulonic acid | 185.20 |
| Sodium hydroxide, concentrated (30%) | 92.60 |
| Acetic acid, concentrate (100%) | 2.20 |
| Trilon A | 1.00 |
| Formaldehyde, 38% by volume | 1.00 |
| Blue Dye | 0.02 |
| Deionized Water | to 1,000 ml. |

The combination of DAG and sodium hydroxide forms approximately 200 grams of the sodium salt of DAG.

The acetic acid functions to buffer the pH of the composition to 8.5–9.5.

Trilon A is an organic, complex-forming chelating agent (BASF).

| Composition B | |
|---|---|
| Ingredient | grams/liter |
| p-nonylphenoxy poly (oxyethylene) ethanol | 37.5 |
| Trilon A | 1.0 |
| Formaldehyde, 38% by volume | 1.0 |
| Deionized water | to 1,000 ml. |

Other similar surfactants, such as Igepal CO-610, Triton N 101 and Arkopal NO80, can be used in place of the above.

The above compositions are particularly effective on ornamental plants, and, in particular, azaleas.

In such use, the compositions are admixed and diluted as follows:

from September to May    2% Composition A, 1% Composition B and the remainder, deionized water.

| from June to August | 3% Composition A, 1% Composition B and the remainder, deionized water. |

Thus by the judicious use of the two compositions, spray solutions containing different amounts of the active ingredient and the requisite amount of surfactant can be prepared.

EXAMPLE 19

2,3-O-(2-butylidene)-4,6-O-isopropylidene-2-keto-L-gulonic acid

The compound prepared in Example 16, 2,3:4,6-di-O-(2-butylidene)-2-keto-L-gulonic acid, was dissolved in acetone and a catalytic amount of a strong acid, e.g., $HClO_4$ was added. The mixture was stirred until reaction is completed and then the acid was neutralized with $NaHCO_3$. The mixture was filtered and concentrated to crystallize the product, m.p. 91.5°–93.5° C.

EXAMPLE 20

2,3-O-(3-pentylidene)-4,6-O-isopropylidene-2-keto-L-gulonic acid

The compound prepared in Example 15, 2,3:4,6-di-O-(3-pentylidene)-2-keto-L-gulonic acid, was dissolved in acetone and a catalytic amount of a strong acid, e.g., $HClO_4$, was added. The mixture was stirred, until reaction was completed and the acid was then neutralized with $NaHCO_3$. The mixture was filtered and concentrated to crystallize the product.

In like manner, other gulonic acid derivatives are prepared as, for example, 2,3-O-(2-ethylidene)-4,6-O-(isopropylidene)-2-keto-L-gulonic acid from 2,3:4,6-di-O-(2-ethylidene)-2-keto-L-gulonic acid.

What is claimed is:

1. A plant growth regulating composition comprising agriculturally acceptable adjuvants and, as the active ingredient, an amount effective in regulating plant growth of a compound of the formula

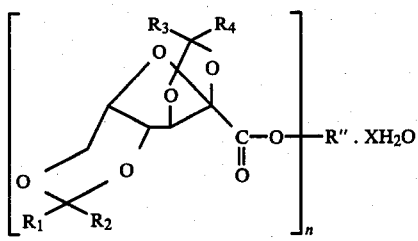

wherein, when n is 1, R″ is hydrogen, sodium, potassium, ammonium, substituted ammonium, straight or branched chain alkyl of from 1 to 20 carbon atoms, straight or branched chain alkenyl of from 2 to 20 carbon atoms, straight or branched chain alkynyl of from 2 to 20 carbon atoms or halo-lower alkyl and, when n is R″, is calcium or lower alkylene; $R_1$, $R_2$, $R_3$ and $R_4$ are hydrogen, straight or branched chain alkyl of from 1 to 7 carbon atoms, straight or branched chain alkenyl of from 2 to 7 carbon atoms, straight or branched chain alkynyl of from 2 to 7 carbon atoms, fluoro-lower alkyl, phenyl or phenyl having one or more substituents selected from the group consisting of alkyl, alkenyl, alkynyl, alkoxy and halo-lower alkoxy; n is an integer from 1 to 2 and X is a number from 0 to 1; enantiomers, racemates and salts thereof, and wherein the agriculturally acceptable adjuvants comprise, in percents by weight of the composition, from about 3% to about 10% of a surfactant, from about 1% to about 5% of an anti-caking compound, from about 0.1% to about 1% of an anti-foaming agent and from about 0.4% to about 1.5% of a buffer.

2. A plant growth regulating composition as in claim 1 wherein $R_1$, $R_2$, $R_3$, and $R_4$ are methyl and, when n is 1, R″ is hydrogen, sodium, potassium, ammonium, diethylammonium, n-ethanol ammonium, straight or branched chain alkyl of from 1 to 12 carbon atoms, straight or branched chain alkenyl of from 2 to 3 carbon atoms or straight or branched chain alkynyl of from 2 to 3 carbon atoms and, when n is 2, R″ is calcium, and wherein the agriculturally acceptable adjuvants comprise, in percents by weight based on the total weight of the composition, from about 3% to about 10% of a surfactant, from about 1% to about 5% of anti-caking compound, from about 0.1% to about 1% of an anti-foaming agent and from about 0.4% to about 1.5% of a buffer.

3. A plant growth regulating composition as in claim 1 wherein the agriculturally acceptable adjuvants comprise about 6% of sodium lauryl sulfate surfactant, about 2.5% of a silicagel anticaking agent, about 0.5% of sodium stearate antifoaming agent and about 1% of anhydrous sodium carbonate buffer.

4. A plant growth regulating composition as in claim 2 wherein the agriculturally acceptable adjuvants comprise about 6% of sodium lauryl sulfate surfactant, about 2.5% of a silicagel anticaking agent, about 0.5% of sodium stearate antifoaming agent and about 1% of anhydrous sodium carbonate buffer.

5. A plant growth regulating composition as in claim 1 wherein the agriculturally acceptable adjuvant comprises a surfactant.

6. A plant growth regulating composition as in claim 2 wherein the agriculturally acceptable adjuvant is a surfactant.

7. A plant growth regulating composition comprising agriculturally acceptable adjuvants and as the active ingredient propargyl 2,3:4,6-di-O-isopropylidene-2-keto-L-gulonate.

8. A plant growth regulating composition comprising agriculturally acceptable adjuvants and as the active ingredient n-pentyl 2,3:4,6-di-O-isopropylidene-2-keto-L-gulonate.

9. A sprayable aqueous solution for use in plant growth regulation which comprises an amount of the composition of claim 1 which is effective in plant growth regulation.

10. A sprayable aqueous solution for use in plant growth regulation which comprises an amount of the composition of claim 2 which is effective in plant growth regulation.

11. A sprayable aqueous solution for use in plant growth regulation which comprises an amount of the composition of claim 3 which is effective in plant growth regulation.

12. A sprayable aqueous solution for use in plant growth regulation which comprises an amount of the composition in claim 4 which is effective in plant growth regulation.

13. A sprayable aqueous solution for use in plant growth regulation which comprises an amount of the composition of claim 5 which is effective in plant growth regulation.

14. A sprayable aqueous solution for use in plant growth regulation which comprises an amount of the composition of claim 6 which is effective in plant growth regulation.

15. A method of regulating plant growth which comprises applying, to the plant to be controlled, an amount, which is effective in plant growth regulation, of a composition comprising agriculturally acceptable adjuvants and, as the active ingredient, an amount effective in regulating plant growth of a compound of the formula

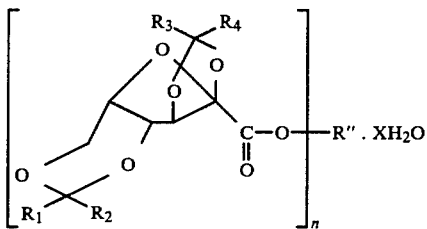

wherein, when n is 1, R" is hydrogen, sodium, potassium, ammonium, substituted ammonium, straight or branched chain alkyl of from 1 to 20 carbon atoms, straight or branched chain alkenyl of from 2 to 20 carbon atoms, straight or branched chain alkynyl of from 2 to 20 carbon atoms or halo-lower alkyl and, when n is R" is calcium or lower alkylene; $R_1$, $R_2$, $R_3$ and $R_4$ are hydrogen, straight or branched chain alkyl of from 1 to 7 carbon atoms, straight or branched chain alkenyl of from 2 to 7 carbon atoms, straight or branched chain alkynyl of from 2 to 7 carbon atoms, fluoro-lower alkyl, phenyl or phenyl having one or more substituents selected from the group consisting of alkyl, alkenyl, alkynyl, alkoxy and halo-lower alkoxy; n is an integer from 1 to 2 and X is a number from 0 to 1; enantiomers, racemates and salts thereof.

16. A method of regulating plant growth which comprises applying, to the plant to be controlled, an amount, which is effective in plant growth regulation, of a composition as in claim 15 wherein $R_1$, $R_2$, $R_3$, and $R_4$ are methyl and, when n is 1, R" is hydrogen, sodium, potassium, ammonium, diethylammonium, n-ethanol ammonium, straight or branched chain alkyl of from 1 to 12 carbon atoms, straight or branched chain alkenyl of from 2 to 3 carbon atoms or straight or branched chain alkynyl of from 2 to 3 carbon atoms and, when n is 2, R" is calcium.

17. A method of regulating plant growth which comprises applying to the plant to be controlled, an amount, which is effective in plant growth regulation, of a composition as in claim 15 wherein the agriculturally acceptable adjuvants comprise, in percents by weight based on the total weight of the composition, from about 3% to about 10% of a surfactant, from about 1% to about 5% of an anti-caking compound, from about 0.1% to about 1% of an antifoaming agent and from about 0.4% to about 1.5% of a buffer.

18. A method of regulating plant growth which comprises applying to the plant to be controlled, an amount, which is effective in plant growth regulation, of a composition as in claim 16 wherein the agriculturally acceptable adjuvants comprise, in percents by weight based on the total weight of the composition, from about 3% to about 10% of a surfactant, from about 1% to about 5% of an anti-caking compound, from about 0.1% to about 1% of an antifoaming agent and from about 0.4% to about 1.5% of a buffer.

19. A method of regulating plant growth which comprises applying to the plant to be controlled, an amount, which is effective in plant growth regulation, of a composition as in claim 15 wherein the agriculturally acceptable adjuvants comprise about 6% of sodium lauryl sulfate surfactant, about 2.5% of a silica-gel anti-caking agent, about 0.5% of sodium stearate antifoaming agent and about 1% of anhydrous sodium carbonate buffer.

20. A method of regulating plant growth which comprises applying to the plant to be controlled, an amount, which is effective in plant growth regulation, of a composition as in claim 16 wherein the agriculturally acceptable adjuvants comprise about 6% of sodium lauryl sulfate surfactant, about 2.5% of a silicagel anticaking agent, about 0.5% of sodium stearate antifoaming agent and about 1% of anhydrous sodium carbonate buffer.

21. A method of regulating plant growth which comprises applying to the plant to be controlled, an amount, which is effective in plant growth regulation, of a composition as in claim 15 wherein the agriculturally acceptable adjuvant comprises a surfactant.

22. A method of regulating plant growth which comprises applying to the plant to be controlled, an amount, which is effective in plant growth regulation, of a composition as in claim 16 wherein the agriculturally acceptable adjuvant is a surfactant.

23. The method of claim 16 wherein the compound is 2,3:4,6-di-O-isopropylidene-2-keto-L-gulonic acid monohydrate.

24. The method of claim 16 wherein the compound is sodium 2,3:4,6-di-O-isopropylidene-2-keto-L-gulonate.

25. The method of claim 16 wherein the compound is potassium 2,3:4,6-di-O-isopropylidene-2-keto-L-gulonate.

26. The method of claim 16 wherein the compound is ammonium 2,3:4,6-di-O-isopropylidene-2-keto-L-gulonate.

27. The method of claim 16 wherein the compound is calcium 2,3:4,6-di-O-isopropylidene-2-keto-L-gulonate.

28. The method of claim 16 wherein the compound is propargyl 2,3:4,6-di-O-isopropylidene-2-keto-L-gulonate.

29. The method of claim 16 wherein the compound is n-pentyl 2,3:4,6-di-O-isopropylidene-2-keto-L-gulonate.

30. The method of claim 16 wherein the compound is dimethylammonium 2,3:4,6-di-O-isopropylidene-2-keto-L-gulonate.

31. The method of claim 16 wherein the compound is N-ethanolammonium 2,3:4,6-di-O-isopropylidene-2-keto-L-gulonate.

* * * * *